United States Patent [19]

Gutman

[11] 4,096,273

[45] Jun. 20, 1978

[54] 3-BENZYL-5-[2-(4-CHLOROPHENYL)3-METHYL BUTYRYLOXY ALKYL] OXADIAZOLE INSECTICIDES

[75] Inventor: Arnold D. Gutman, Berkeley, Calif.

[73] Assignee: Stauffer Chemical Company, Westport, Conn.

[21] Appl. No.: 796,776

[22] Filed: May 13, 1977

[51] Int. Cl.² .................... A01N 9/22; C07D 271/06
[52] U.S. Cl. ............................... 424/272; 260/307 G
[58] Field of Search .................. 260/307 G; 424/272

[56] References Cited

U.S. PATENT DOCUMENTS 3,879,407   4/1975   Hagarty ........................ 260/302 D Primary Examiner—Raymond V. Rush
Attorney, Agent, or Firm—Edwin H. Baker

[57] ABSTRACT

Compounds of the formula

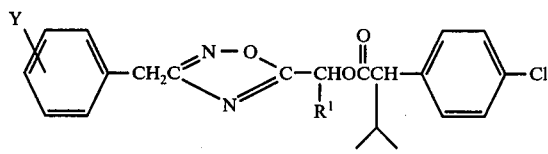

in which $R^1$ is hydrogen or alkyl having 1 to 4 carbon atoms and Y is hydrogen or chlorine, useful as insecticides.

15 Claims, No Drawings

3-BENZYL-5-[2-(4-CHLOROPHENYL)3-METHYL BUTYRYLOXY ALKYL] OXADIAZOLE INSECTICIDES

This invention relates to certain novel chemical compounds and their use as insecticides. More particularly, this invention relates to certain novel 3-benzyl-5-[2-(4-chlorophenyl) 3-methyl butoxy alkyl] oxadiazole which are useful as insecticides.

The compounds of the present invention that are useful as insecticides are those having the structural formula

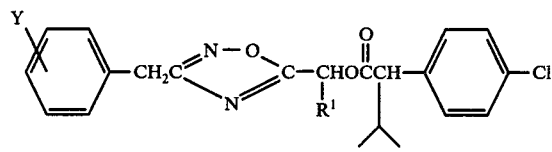

in which $R^1$ is hydrogen or alkyl having 1 to 4 carbon atoms, preferably methyl, and Y is hydrogen or chlorine. Preferably Y is hydrogen.

The compounds of this invention can be prepared according to the following reaction steps:

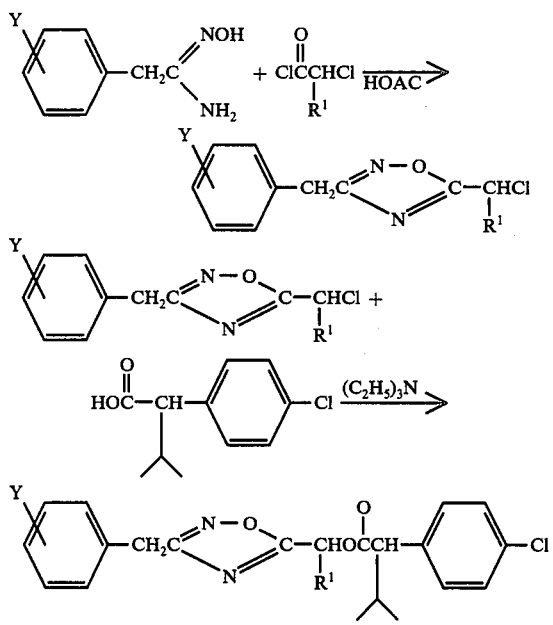

The term "alkyl having 1 to 4 carbon atoms" includes methyl, ethyl, n-propyl, isopropyl, n-butyl, isobutyl, t-butyl and sec.-butyl.

Preferably, reaction step 1 is carried out by heating a solution of the reactants in acetic acid at reflux until hydrogen chloride gas evolution ceases. Generally, about equimole amounts of the reactants are used. The reaction product is recovered and purified by conventional procedures.

Preferably, reaction step 2 is carried out by heating under reflux equimole amounts of the reactants with a hydrochloride acceptor such as triethylamine in a solvent such as methylethylketone. After the reaction is complete, the reaction product is recovered and purified by conventional techniques.

The synthesis of the compounds of this invention is specifically illustrated in the following examples.

EXAMPLE I
3-BENZYL-5-CHLOROMETHYL-1,2,4-OXADIAZOLE

This example teaches the synthesis of a representative intermediate of reaction step 1.

First, 15 grams (0.1 mole) of $C_6H_5$—$CH_2C(NH_2)$=NOH, 11.3 grams (0.1 mole) of chloroacetylchloride and 20 milliliters of acetic acid were combined in a 100 milliliter round bottom flask and were heated under reflux until the HCl evolution had ceased. The mixture was then cooled and poured into 150 milliliters of saturated $NaHCO_3$ solution. The aqueous mixture was extracted with 2–150 milliliter portions of benzene. The benzene phase was then combined, treated with activated carbon, dried with $MgSO_4$, filtered, and evaporated in vacuo to yield 10.6 grams (50% of theory) of the desired intermediate.

EXAMPLE II
3-BENZYL-5-[2-(4-CHLOROPHENYL)3-METHYL BUTOXYMETHYL]1,2,4-OXADIAZOLE

This example teaches the synthesis of a representative compound of reaction step 2 using the intermediate prepared in Example I.

First, 2.1 grams (0.01 mole) of the intermediate of Example I, 2.3 grams (0.011 mole) of 2-(4-chlorophenyl)3-methyl butyric acid, 1.0 grams (0.01 mole) of triethylamine, and 100 milliliters of methylethylketone were combined and heated under reflux for 2 hours. The mixture was then cooled and poured into 200 milliliters of benzene. The benzene mixture was then washed in turn with 100 milliliters of $H_2O$, 100 milliliters of 5% $K_2CO_3$ solution, and 100 milliliters of $H_2O$. The benzene phase was then dried with $MgSO_4$ and evaporated in vacuo to yield 3.0 grams (78% of theory) of the desired product. $n_D^{30}$ 1.5210.

The following is a table of certain selected compounds that are preparable according to the procedure described hereto. Compound numbers are assigned to each compound and are used throughout the remainder of the specification.

TABLE I

| Compound Number | $R^1$ | Y | $n_D^{30}$ |
|---|---|---|---|
| 1[a] | H | H | 1.5210 |
| 2 | H | 2-Cl | 1.5270 |
| 3 | H | 3-Cl | 1.5246 |
| 4 | $CH_3$ | H | 1.5026 |

[a] Prepared in Example II

Insecticidal Evaluation Tests

The compounds of Table I were found to have insecticidal activity against the following insect species which were used in the evaluation tests described hereafter.

1. Housefly (HF) — *Musca domestica* (Linn.)
2. Black Bean Aphid (BBA) — *Aphis fabae* (Scop.)
3. Green Peach Aphid (GPA) — *Myzus persicae* (Sulzer)

4. Saltmarsh Caterpiller (SMC) — *Estigmene acrea* (Drury)
5. Cabbage Looper (CL) — *Trichoplusia ni* (Hubner)
6. Tobacco Budworm (TBW) — *Heliothis virescens* (F.)
7. Southern House Mosquito (MOS) — *Culex pipiens quinquefasciatus* (Say)
8. German Cockroach (GR) — *Blattella germanica* (Linn.)
9. Lygus Bug (LB) — *Lygus hesperus* (Knight)

The insecticidal evaluation tests were conducted as follows:

Housefly: Test compounds were diluted in acetone and aliquots pipetted onto the bottom of 55 × 15 millimeter aluminum dishes. To insure even spreading of the chemical on the bottom of the dishes, one milliliter of acetone containing 0.02% peanut oil was also added to each dish. After all solvents had evaporated, the dishes were placed in circular cardboard cages containing 25 female houseflies, one to two days old. The cages were covered on the bottom with cellophane and on top with tulle netting, and each contained a sugar-water saturated cotton plug for maintenance of the flies. Mortality was recorded after 48 hours. Test levels ranged from 100 μg/25 female houseflies down to that at which approximately 50% mortality occurred. The $LD_{50}$ values are expressed below in Table II under the heading "HF" in terms of μg of the test compound per 25 female flies.

Black Bean Aphid: Nasturtium plants (*Tropaeolum sp.*), approximately five centimeters tall, were transplanted into sandy loam soil in three-inch clay pots and infested with 25-50 black bean aphids of mixed ages. Twenty-four hours later they were sprayed to the point of runoff with 50—50 acetone-water solutions of the test chemicals. Treated plants were held in the greenhouse and mortality was recorded after 48 hours. Test concentrations ranged from 0.05% down to that at which 50% mortality occurred. $LD_{50}$ values are expressed below in Table II under the heading "BBA" in terms of percent of the test compound in the sprayed solution.

Green Peach Aphid: Radish plants (*Rhaphanus sativus*), approximately two centimeters tall, were transplanted into sandy loam soil in three-inch clay pots and infested with 25-50 green peach aphids of mixed ages. Twenty-four hours later they were sprayed to the point of runoff with 50—50 acetone-water solutions of the test chemicals. Treated plants were held in the greenhouse and mortality was recorded after 48 hours. Test concentrations ranged from 0.05% down to that at which 50% mortality occurred. $LD_{50}$ values are expressed below in Table II under the heading "GPA" in terms of percent of the test compound in the sprayed solution.

Saltmarsh Caterpillar: Test compounds were diluted in a 50—50 acetone-water solution. Sections of curly dock (*Rumex crispus*) leaves, approximately 1 × 1.5 inches, were immersed in the test solution for two-three seconds and placed on a wire screen to dry. The dried leaves were placed in petri dishes containing a moistened piece of filter paper and infested with five second-instar saltmarsh caterpillar larvae. Mortality of the larvae was recorded 48 hours later, and a piece of synthetic media was added to dishes containing survivors. These were then held for five additional days to observe for any delayed effects of the test chemicals. Test concentrations ranged from 0.05% down to that at which approximately 50% mortality occurred. $LD_{50}$ values are expressed below in Table II under the heading "SMC" in terms of percent of the test compound in the solution.

Cabbage Looper: Test compounds were diluted in a 50—50 acetone-water solution. Cotyledons of hyzini squash (*Calabacita abobrinha*), approximately 1 × 1.5 inches, were immersed in the test solutions for two-three seconds and placed on a wire screen to dry. The dried leaves were placed in petri dishes containing a moistened piece of filter paper and infested with five second-instar cabbage looper larvae. Mortality of the larvae was recorded 48 hours later, and a piece of synthetic media added to dishes containing survivors. These were then held for five additional days to observe for any delayed effects of the test chemicals. Test concentrations ranged from 0.1% to that at which approximately 50% mortality occurred. $LD_{50}$ values are expressed below in Table II under the heading "CL" in terms of percent of the test compound in the solution.

Tobacco Budworm: Test compounds were diluted in a 50—50 acetone-water solution. Sections of Romaine lettuce (*Latuca sativa*) leaves, approximately 1 × 1.5 inches, were immersed in the test solutions for two-three seconds and placed on a wire screen to dry. The dried leaves were placed in petri dishes containing a moistened piece of filter paper and infested with five second-instar tobacco budworm larvae. Mortality of the larvae was recorded 48 hours later, and a piece of synthetic media added to dishes containing survivors. These were then held for five additional days to observe for any delayed effects of the test chemicals. Test concentrations ranged from 0.1% to that at which approximately 50% mortality occurred. $LD_{50}$ values are expressed below in Table II under the heading "TBW" in terms of percent of the test compound in the solution.

Southern House Mosquito Larvae (*Culex pipiens quinquefasciatus* Say): Insecticidal activity was determined using third instar larvae of the mosquito (*Culex pipiens quinquefasciatus*). Ten larvae were placed in a six ounce paper cup containing 100 milliliters of an aqueous solution of the test chemical. The treated larvae were stored at 70° F. and 48 hours later the mortality was recorded. Test concentrations ranged from one ppm down to that at which approximately 50% mortality occurred. $LD_{50}$ values are expressed below in Table II under the heading "MOS" in terms of ppm of the test compound in the solution.

German Cockroach: Test compounds were diluted in a 50—50 acetone-water solution. Two centimeters of the solution were sprayed through a DeVilbiss type EGA hand spray gun into circular cardboard cages containing 10 one-month-old German cockroach nymphs. The test cages were covered on the bottom with cellophane and on the top with tulle netting. Percent mortality was recorded seven days later. Test concentrations ranged from 0.1% down to that at which approximately 50% mortality occurred. $LD_{50}$ values are expressed below in Table II under the heading "GR" in terms of percent of the test compound in the sprayed solution.

Lygus Bug: Test compounds were diluted in a 50—50 acetone-water solution. Two centimeters of the solution were sprayed through a DeVilbiss type EGA hand spray gun into circular cardboard cages containing one string bean pod and 10 adult lygus bugs. The test cages were covered on the bottom with cellophane and on the top with tulle netting. Percent mortality was recorded 48 hours later. Test concentrations ranged from 0.05% down to that at which approximately 50% mortality occurred. LD$_{50}$ values are expressed below in Table II under the heading "LB" in terms of percent of the test compound in the sprayed solution.

TABLE II

| Compound Number | HF (μg) | BBA (%) | GPA (%) | SMC (%) | CL (%) | TBW (%) | MOS (ppm) | GR (%) | LB (%) |
|---|---|---|---|---|---|---|---|---|---|
| 1 | 6.6 | .001 | .002 | .003 | .01 | .01 | .04 | .08 | .03 |
| 2 | 8.9 | .01 | .003 | .03 | .008 | — | .03 | .10 | — |
| 3 | 62. | — | — | .05 | .03 | — | — | — | — |
| 4 | 35. | .008 | .05 | .05 | .02 | .1 | .2 | .1 | — |

The compounds of this invention are generally formulated into a form suitable for convenient application. For example, the compounds can be prepared into a pesticidal composition in the form of emulsions, suspensions, solutions, dusts or aerosol sprays. In general, such pesticidal compositions will contain, in addition to the active compound, the inert adjuvants which are found normally in pesticide preparations. In these compositions, an active compound of this invention can be employed as the sole pesticide component or it can be used in an admixture with other compounds having similar utility.

The pesticide compositions of this invention can contain, (a) liquid adjuvants, such as organic solvents, sesame oil, xylene range solvents, heavy petroleum, etc.; water; (b) emulsifying agents; (c) surface active agents; (d) solid adjuvants such as talc; pyrophyllite, diatomite; gypsum; clays or (e) propellants, such as dichlorodifluoromethane, etc.

If desired, however, the active compounds can be applied directly to feedstuffs, seeds, etc., or upon other materials upon which the pests feed. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, and emulsion, suspension, or aerosol spray. While the concentration of the active compound in the aforesaid compositions can vary within wide limits, ordinarily the active compound will comprise between about 1 and about 95% by weight of the pesticidal composition and more preferably between about 5 to 80% by weight.

I claim:

1. A compound of the formula

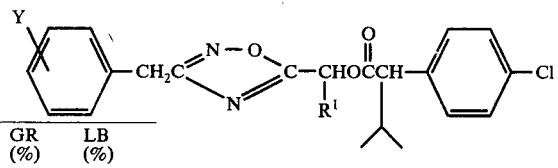

in which $R^1$ is hydrogen and Y is hydrogen, 2-chloro or 3-chloro, or $R^1$ is methyl and Y is hydrogen.

2. The compound of claim 1 in which $R^1$ is hydrogen and Y is hydrogen.

3. The compound of claim 1 in which $R^1$ is hydrogen and Y is 2-chloro.

4. The compound of claim 1 in which $R^1$ is hydrogen and Y is 3-chloro.

5. The compound of claim 1 in which $R^1$ is methyl and Y is hydrogen.

6. A pesticidal composition comprising a compound of the formula

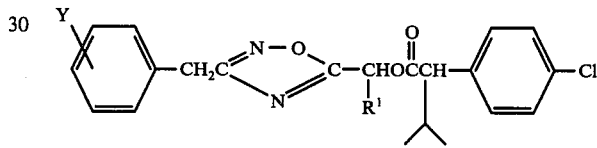

in which $R^1$ is hydrogen and Y is hydrogen, 2-chloro or 3-chloro, or $R^1$ is methyl and Y is hydrogen and an inert adjuvant.

7. The pesticidal composition of claim 6 in which $R^1$ hydrogen and Y is hydrogen.

8. The pesticidal composition of claim 6 in which $R^1$ is hydrogen and Y is 2-chloro.

9. The pesticidal composition of claim 6 in which $R^1$ is hydrogen and Y is 3-chloro.

10. The pesticidal composition of claim 6 in which $R^1$ is methyl and Y is hydrogen.

11. A method of controlling insects comprising applying to the habitat thereof an insecticidally effective amount of a compound of the formula

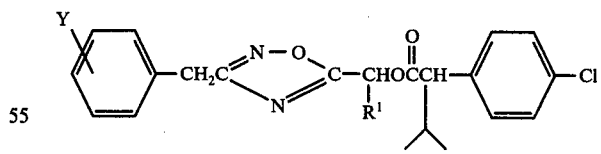

in which $R^1$ is hydrogen and Y is hydrogen, 2-chloro or 3-chloro, or $R^1$ is methyl and Y is hydrogen.

12. The method of claim 11 in which $R^1$ is hydrogen and Y is hydrogen.

13. The method of claim 11 in which $R^1$ is hydrogen and Y is 2-chloro.

14. The method of claim 11 in which $R^1$ is hydrogen and Y is 3-chloro.

15. The method of claim 11 in which $R^1$ is methyl and Y is hydrogen.

* * * * *